(12) United States Patent
Zhou et al.

(10) Patent No.: US 6,735,372 B2
(45) Date of Patent: May 11, 2004

(54) CHANNEL POWER MONITOR

(75) Inventors: Dennis Chi Zhou, Cupertino, CA (US);
Kai Zhang, San Jose, CA (US);
Shou-Jong Sheih, Saratoga, CA (US)

(73) Assignee: Arasor Corporation, Mountain View, CA (US)

( * ) Notice: Subject to any disclaimer, the term of this patent is extended or adjusted under 35 U.S.C. 154(b) by 114 days.

(21) Appl. No.: 10/163,153

(22) Filed: Jun. 4, 2002

(65) Prior Publication Data

US 2003/0210885 A1 Nov. 13, 2003

Related U.S. Application Data

(60) Provisional application No. 60/378,721, filed on May 7, 2002.

(51) Int. Cl.[7] .............................................. G02B 6/00
(52) U.S. Cl. ........................................ 385/140; 385/147
(58) Field of Search ................................. 385/140, 147

(56) References Cited

U.S. PATENT DOCUMENTS 4,516,827 A * 5/1985 Lance et al. ................ 385/140
5,432,875 A * 7/1995 Korkowski et al. ........... 385/27
5,900,983 A * 5/1999 Ford et al. .................. 359/627
6,144,793 A * 11/2000 Matsumoto et al. ........ 385/140

* cited by examiner

Primary Examiner—John D. Lee
Assistant Examiner—Jennifer Doan
(74) Attorney, Agent, or Firm—Lumen Intellectual Property Services, Inc.

(57) ABSTRACT

The present invention is directed towards a channel power monitor for monitoring channel power levels for each of N signal channels. The value of each channel power level is designated as $p(\lambda_i)$, where $\lambda_i$ is a channel parameter that characterizes each channel. An embodiment of the invention includes a variable channel attenuator having M attenuation profiles where $M \geq N$, and where a k-th attenuation profile is characterized as a function of the channel parameter $\lambda_i$ by $A_k(\lambda_i)$. This embodiment also includes a detector for measuring a k-th integrated attenuated power level, the value of which is represented by $P_k$. An analysis unit receives all of the values $P_k$ of the integrated attenuated power levels and thereupon derives the values $p(\lambda_i)$ of the channel power levels by solving a set of linear equations.

34 Claims, 4 Drawing Sheets

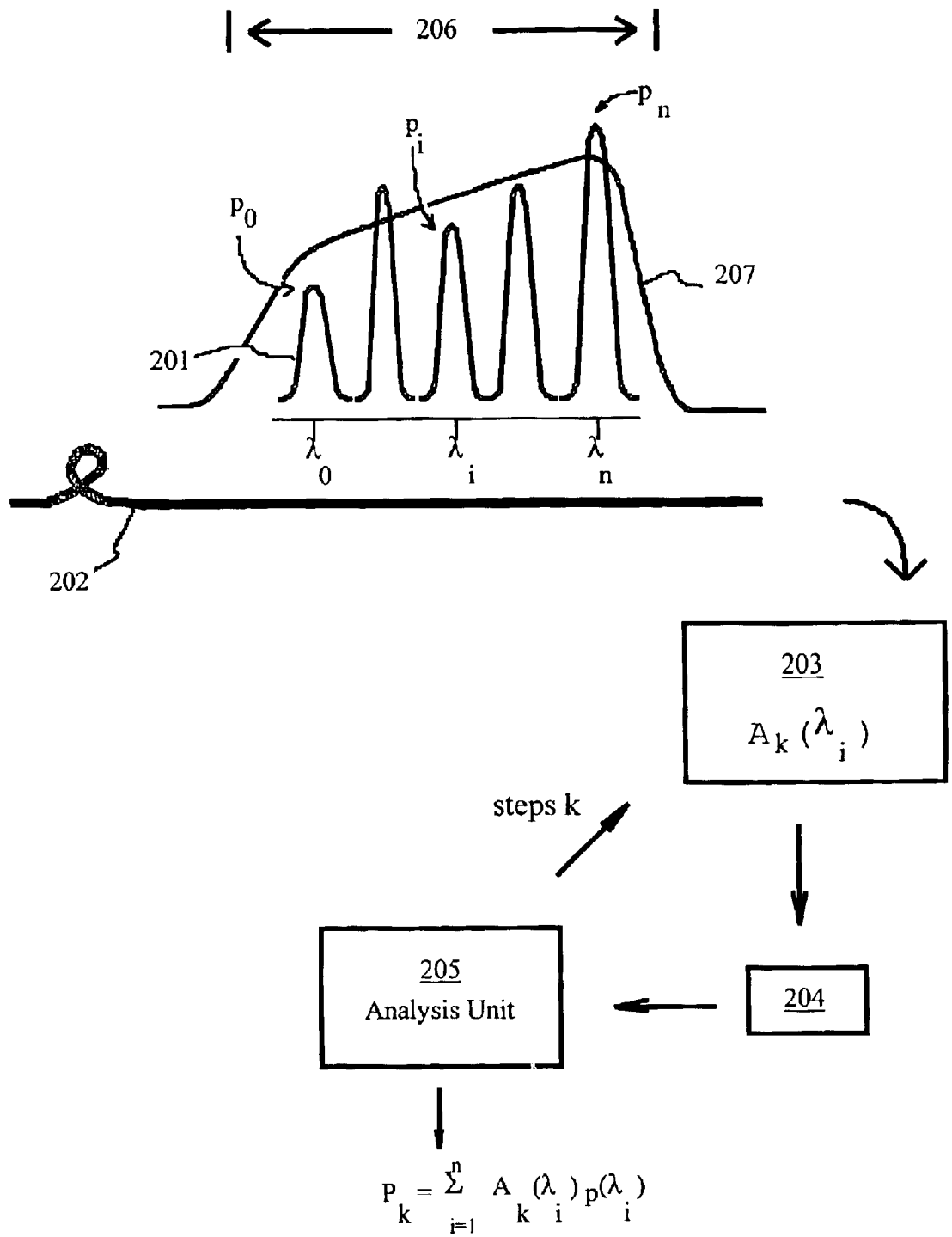

CHANNEL POWER MONITOR

CROSS-REFERENCE TO RELATED APPLICATIONS

This application claims priority under USC 119(e) of provisional patent application Ser. No. 60/378,721 filed May 7, 2002, entitled "Channel Power Monitor," which is hereby incorporated by reference in its entirety.

FIELD OF THE INVENTION

The present invention relates generally to monitoring the channel power levels of communication signals. More specifically, the invention relates to the monitoring of optical signals in optical fiber telecommunication systems and networks, particularly to the case in which the monitoring is accomplished with a channel power monitor based on a variable optical channel attenuator.

BACKGROUND OF THE INVENTION

In modern fiber optic telecommunication systems and networks, the signals are transmitted along optical fibers. Each optical fiber can carry an independent signal in each of multiple signal channels. The signal in an optical fiber typically requires periodic amplification to maintain appropriate signal strength. To properly amplify the signal, smart amplifiers routinely require information regarding the channel power level in each of the channels transmitted by the fiber. In optical systems, each channel is characterized by a wavelength that is representative of the wavelengths in the channel. A diffraction-grating spectrum analyzer or a Fabry-Perot spectrometer could be used to determine the channel power levels, but these devices tend to be costly. What is desired is a channel power monitor that can easily be made low-cost, small and compact.

SUMMARY OF THE INVENTION

The current invention provides an apparatus and method for the monitoring channel power levels in a number of signal channels. Although the invention was motivated by the need to monitor the channel power levels in optical fiber systems, the invention is not restricted to the optical range of the electromagnetic spectrum, or even to electromagnetic signals, but can be applied generally to any system with multiple channels that require monitoring.

Various embodiments of the invention involve methods for monitoring channel power levels of input signals. Each of N signal channels is characterized by a channel parameter $\lambda_i$, where i is an index in the range $1 \leq i \leq N$. The value of each channel power level is designated as $p(\lambda_i)$.

In one embodiment a set of M attenuation profiles is provided, where $M \geq N$. Each attenuation profile is characterized as a function of the channel parameter $\lambda_i$ by a k-th attenuation profile $A_k(\lambda_i)$, and k is a profile index. The profile index k is initialized to a value of 1. An input signal is attenuated according to the k-th attenuation profile $A_k(\lambda_i)$, thereby producing an attenuated power level in each signal channel. A k-th integrated attenuated power level is measured. The k-th integrated attenuated power level is the attenuated power level integrated over the N signal channels after application of the k-th attenuation profile. The value of the k-th integrated attenuated power level is represented by $P_k$. The index k is then incremented by 1 and the attenuating, measuring, and incrementing steps are then repeated until k>M. M values of $P_k$ are then available. Because the $M \geq N$ and all the $A_k(\lambda_i)$ are known, the following set of linear equations are solved for $p(\lambda_i)$:

$$P_k = \sum_{i=1}^{N} A_k(\lambda_i) p(\lambda_i)$$

for $1 \leq k \leq M$.

In another embodiment the input signal is split into M substantially identical scaled input signals represented by $r(\lambda_i)$, where $r(\lambda_i) = \alpha(\lambda_i) p(\lambda_i)$ and $\alpha(\lambda_i)$ is a known scaling function. Each scaled input signal is attenuated according to a different attenuation profile $A_k(\lambda_i)$, thereby producing M attenuated power levels for each signal channel. M integrated attenuated power levels are measured, the value of the k-th integrated attenuated power level being represented by $P_k$. The following set of linear equations are solved for $r(\lambda_i)$ $$P_k = \sum_{i=1}^{N} A_k(\lambda_i) r(\lambda_i)$$

for $1 \leq k \leq M$. The channel power level $p(\lambda_i)$ is determined from $p(\lambda_i) = r(\lambda_i)/\alpha(\lambda_i)$.

An apparatus for monitoring channel power levels includes a variable channel attenuator that has multiple attenuation profiles. The apparatus further includes a detector for measuring integrated attenuated power levels, and an analysis unit that receives all of the values of the integrated attenuated power levels. The analysis unit solves a set of linear equations to obtain the values of the channel power levels.

An alternative apparatus includes a splitter for splitting the input signal into M scaled input signals. The scaled input signals are then attenuated by any appropriate means, whether that be a variable channel attenuator, multiple individual attenuators, or some other means. Multiple detectors are preferably used to measure the integrated attenuated power levels. The analysis unit solves modified equations to determine the values of the channel power levels.

Additional features and advantages of the invention will be set forth in part in the description that follows, and in part will be obvious from the description, or may be learned by practice of the invention. Various embodiments of the invention do not necessarily include all of the stated features or achieve all of the stated advantages.

BRIEF DESCRIPTION OF THE DRAWINGS

The accompanying drawings illustrate a complete embodiment of the invention according to the best modes so far devised for the practical application of the principles thereof, and in which:

FIG. 2 is an embodiment of a channel power monitoring system.

DETAILED DESCRIPTION OF PREFERRED EMBODIMENTS

Figure 1A:
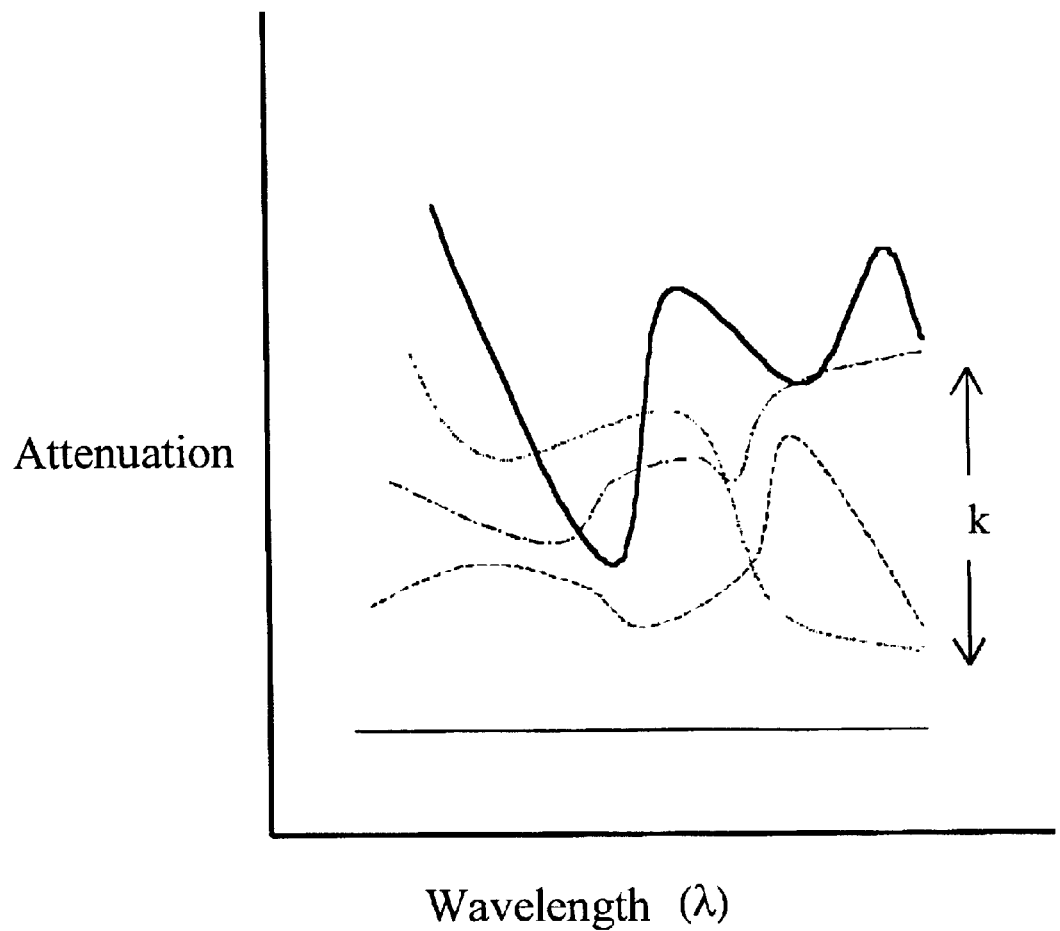
FIG. 1A is a graph of attenuation versus λ for a typical variable optical channel attenuator.
Figure 1B:
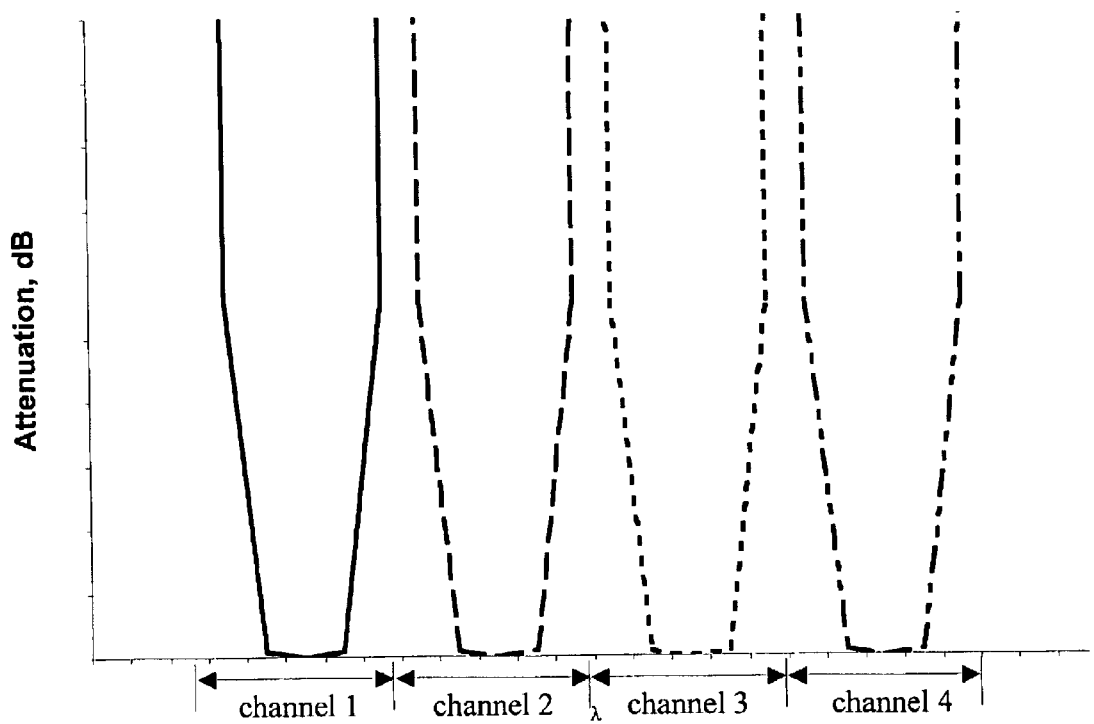
FIG. 1B is a graph of attenuation versus λ for attenuation profiles that sparingly attenuate signals in one channel and very significantly attenuate signals in all other channels.
Figure 1C:
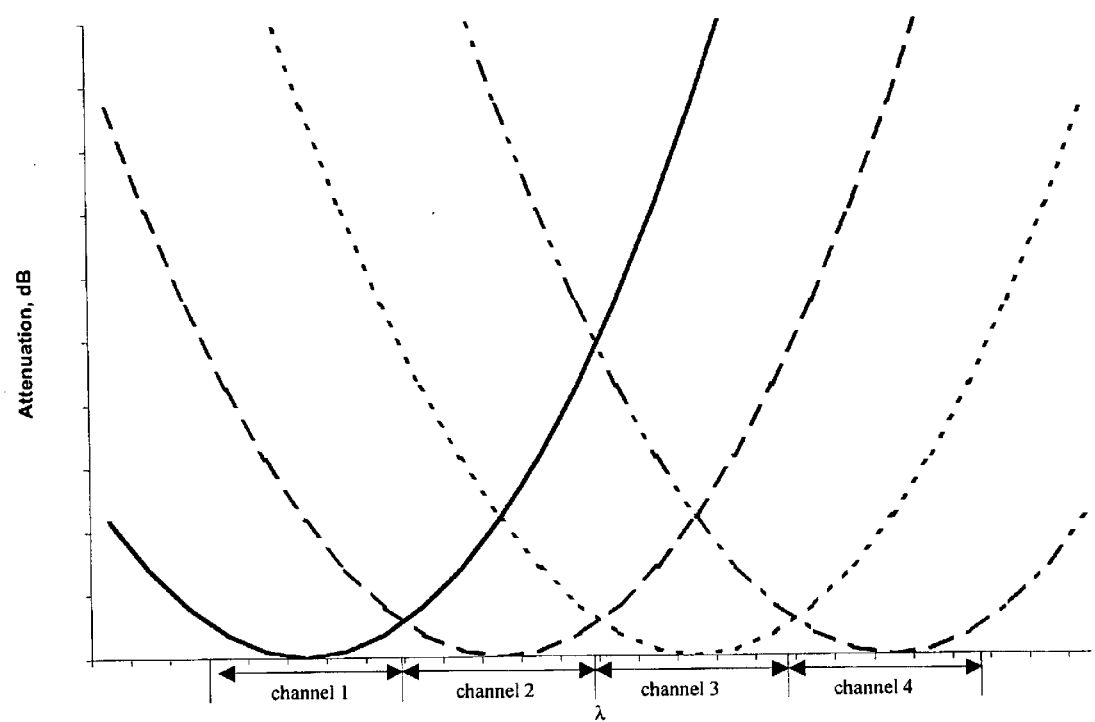
FIG. 1C is a graph of attenuation versus λ for attenuation profiles that sparingly attenuate signals in one channel and more significantly attenuate signals in neighboring channels.

Referring now to the drawings, where similar elements are numbered the same, FIGS. 1A–C depict sets of curves that represent attenuation profiles for different profile indices, k. For the purposes of this application, an attenuation profile is defined as the ratio of output power to input power as a function of a parameter $\lambda$. The k-th attenuation profile is represented by $A_k(\lambda)$. To be consistent with accepted practices, the attenuation profiles shown in FIGS. 1A–C are plotted as the negative of 10 times the base-10 logarithm of the output power to input power ratio. Therefore, large values of attenuation on the plots correspond to small ratios of output power to input power. However, the function $A_k(\lambda)$ (and its discrete counterpart discussed below) should always be understood to be the ratio of output power to input power.

The most preferred embodiments of the instant invention are concerned with channel power monitors for optical signals propagating in an optical fiber. Hence, the parameter $\lambda$ (and its discrete counterpart discussed below) will typically refer to wavelength. In modern telecommunication systems and networks, the signals are often transmitted along optical fibers. Each optical fiber can carry an independent signal in each of multiple signal channels. The signal channels can span the conventional C-band (1530 to 1565 nm) or the long wavelength L-band (1565 to 1625 nm) or any desired portion of the optical spectrum. The instant invention involves the use of variable channel attenuation to monitor the channel power levels.

In general each discrete channel is characterized by a discrete channel parameter $\lambda_i$ that is representative of the range of the parameter $\lambda$ in the i-th channel. The discrete function $A_k(\lambda_i)$ characterizes the continuous attenuation profile $A_k(\lambda)$. The characterization could take many forms. For instance $A_k(\lambda_i)$ could be the value of the continuous function $A_k(\lambda)$ at the point $\lambda=\lambda_i$. However, most preferably, $A_k(\lambda_i)$ represents the value of the output power to input power ratio integrated over the range of $\lambda$ in the i-th channel.

The objective of the invention is to monitor the channel power levels of input signals for each of N signal channels. Each channel power level has a value designated as $p(\lambda_i)$, where each of the N signal channels is designated by an index i, and $1 \leq i \leq N$.

A set of M attenuation profiles is provided. Each attenuation profile is characterized as a function of the channel parameter $\lambda_i$ by a k-th attenuation profile $A_k(\lambda_i)$. Note that $M \geq N$.

In preferred embodiments, the profile index k is initialized to a value of 1. An input signal is attenuated according to the k-th attenuation profile $A_k(\lambda_i)$. This produces an attenuated power level in each signal channel.

The attenuated power level integrated over the N signal channels is measured. The value of the k-th integrated attenuated power level is represented by $P_k$. Mathematically, the integrated attenuated power level is represented by:

$$P_k = \sum_{i=1}^{N} A_k(\lambda_i) p(\lambda_i)$$

This expression is exact if $A_k(\lambda_i)$ represents the value of the output power to input power ratio integrated over the range of $\lambda$ in the i-th channel and $p(\lambda_i)$ represents the value of the input power integrated over the range of $\lambda$ in the i-th channel. With other definitions of $A_k(\lambda_i)$ and $p(\lambda_i)$, the expression is approximate. However, because the approximation is often very good, for the purposes of this document, both the approximate and exact cases will be treated the same and an equals sign (=) will continue to be used. Similarly, in other portions of this document, very good physical approximations are often represented by exact mathematical expressions.

In practice, measuring the integrated attenuated power level is often quite straightforward. For instance, many photodetectors produce an output signal that is easily related to the total power integrated over a range of wavenumbers. A properly selected photodetector will therefore provide the integrated attenuated power level directly.

After obtaining the integrated attenuated power level, the profile index k is incremented by 1. If fewer than M attenuation profiles have been applied, the process of applying the attenuation profile, measuring the integrated attenuated power level, and incrementing the profile index is repeated. Note that the successive attenuation profiles are not applied to exactly the same input signal, but rather to input signals that are slightly displaced in time. In other words, the input signal that is attenuated by the $k+1^{st}$ attenuation profile is slightly later in time than the input signal that is attenuated by the k-th attenuation profile. The values $p(\lambda_i)$ of the channel power levels are assumed to be substantially the same over the time in which the set of M attenuation profiles are applied.

After all M attenuation profiles are applied, a set of linear equations is obtained:

$$P_k = \sum_{i=1}^{N} A_k(\lambda_i) p(\lambda_i)$$

for $1 \leq k \leq M$. This set of linear equations is solved to obtain $p(\lambda_i)$, the values of the channel power level.

The linear equations can be collected into a simple matrix equation:

$$\begin{pmatrix} A_{11} & \cdots & A_{1N} \\ \vdots & & \vdots \\ A_{M1} & \cdots & A_{MN} \end{pmatrix} \begin{pmatrix} P(\lambda_1) \\ \vdots \\ P(\lambda_N) \end{pmatrix} = \begin{pmatrix} P_1 \\ \vdots \\ P_r \end{pmatrix}$$

where the elements of the matrix are given by $A_{ki}=A_k(\lambda_i)$.

A key to accurate solution of the above equations is to find an attenuation matrix A with a good condition number. The condition number of a matrix A is defined as $$\kappa(A) = \|A\| \cdot \|A^{-1}\|$$

where $\|A\|$ is the norm of matrix A. Any well-defined matrix norm is appropriate, however, the p=2, or spectral norm is preferred. In the ideal situation, the condition number is 1.

For the case in which the number of attenuation profiles M equals the number of signal channels N, a condition number of 1 is achieved with a diagonal matrix. A diagonal matrix is one in which only the diagonal elements $A_{ki}$ where k=i are nonzero. For the purposes of this document, we will also consider a matrix to be diagonal if it can be made diagonal by re-ordering its rows. Similarly, for the purposes of this document, matrices having special characteristics will include those matrices that naturally have those characteristics as well as those that would have those characteristics if the rows were re-ordered. Note that re-ordering the rows corresponds to applying the attenuation profiles in a different order.

A diagonal matrix A corresponds to the case in which each signal channel is associated with an attenuation profile that allowed only signals in that channel to pass, completely or at least substantially attenuating signals in all other channels. FIG. 1B illustrates a set of 4 attenuation profiles that would likely produce a diagonal matrix A for the 4 channels shown. The attenuation is quite significant for all values of λ outside of each channel. Note that the nonzero elements of a diagonal matrix need not all be the same.

Although a diagonal matrix would give a condition number of 1, the required attenuation profiles are difficult to realize at low cost. An attenuation matrix that was diagonally dominant might not necessarily have a condition number of 1, but the condition number of diagonally dominant matrices is typically small, exactly how small would depend upon the size of the matrix and the extent of diagonal dominance. A matrix is diagonally dominant if the absolute value of each diagonal element is greater than the sum of the absolute values of the other elements in its row (or column). FIG. 1C illustrates a set of 4 attenuation profiles that would likely provide an attenuation matrix that was diagonally dominant. Each attenuation profile sparingly attenuates signals within only one band and attenuates signals in other bands more significantly, although not completely.

The attenuation matrix associated with the attenuation profiles of FIG. 1C would also likely be banded, meaning that nonzero elements only appear along the diagonal and in discrete bands parallel to the diagonal. Banded matrices are solved much more efficiently and usually more accurately than full matrices, i.e., those matrices in which elements having a value of zero, or substantially zero, do not appear with any regular pattern. The attenuation profiles shown in FIG. 1C would likely produce a tridiagonal attenuation matrix. A tridiagonal matrix is a special type of banded matrix in which nonzero elements appear only on the diagonal and on one parallel band directly above the diagonal and one parallel band directly below the diagonal. With reference to FIG. 1C, note that each attenuation profile sparingly attenuates signals within one channel, more significantly attenuates signals in each adjacent channel, and very significantly attenuates signals in all other channels. Hence, the corresponding attenuation matrix would have relatively large-valued entries along its diagonal, smaller-valued entries on the bands directly above and below the diagonal, and essentially zero-valued entries elsewhere in the matrix.

Numerous other options exist for choosing the attenuation profiles to facilitate the solution of the equations and all are included within the broad scope of the invention.

Once the attenuation profiles are selected and the attenuation matrix A is determined, the attenuation matrix A can be decomposed into component factors that facilitate the solution of the system of equations. One common full matrix decomposition is known as LU decomposition, where L and U are lower and upper triangular matrices respectively. The factorization can be performed once, as soon as the attenuation matrix A is determined. The entire system of equations can then be readily solved for any values on the right-hand side by first applying a forward substitution followed with a reverse substitution. The forward and reverse substitution steps can be performed quite rapidly. Other types of decomposition can also be performed. The best decomposition will depend upon the characteristics of the matrix A and the implementation details.

Much of the previous discussion with respect to the types of matrices can readily be generalized to nonsquare matrices, i.e., those in which the number of attenuation profiles M exceeds the number of signal channels N. However, special solution techniques may be required when M>N. In these circumstances, the system is overdetermined and either M−N equations are redundant, i.e., linear combinations of other equations, or the system can only be solved with some amount of error. In cases in which M−N equations are found to be redundant, these equations can be removed from the system with no loss of information and the resulting system of N equations and N unknowns can be solved as before. If the equations are not redundant, then some amount of inconsistency is inherent in the system. This inconsistency might be introduced by measurement errors, changes in time of the input signal power, inaccuracies in the characterization of the attenuation profiles, etc. Methods for solving the overdetermined system include eliminating equations with the greatest perceived errors, various types of averaging of the solutions for selected N-by-N systems, or employing a method like linear least squares to try to minimize the error introduced by the inconsistency. All such approaches are considered to be within the scope of the invention.

Another embodiment of the invention ensures that the input signal attenuated by each attenuation profile is substantially the same. In this approach, the input signal is split into M substantially identical scaled input signals with power level represented by $r(\lambda_i)$, where $r(\lambda_i)=\alpha(\lambda_i)p(\lambda_i)$ and $\alpha(\lambda_i)$ is a known scaling function. Each scaled input signal is attenuated according to a different attenuation profile $A_k(\lambda_i)$, thereby producing M attenuated power levels, one for each scaled input signal. Integrated attenuated power levels are measured as before, however in this embodiment, all M integrated attenuated power levels can be measured substantially simultaneously, if desired. Alternatively, with some sort of storage or delay capability, the integrated attenuated power levels can be measured sequentially, as with the previously described embodiments. In the present embodiment, the following set of linear equations are solved for the scaled input signal power $r(\lambda_i)$ $$P_k = \sum_{i=1}^{N} A_k(\lambda_i) r(\lambda_i)$$

for $1 \leq k \leq M$. Then the input channel power level is determined by: $p(\lambda_i)=r(\lambda_i)/\alpha(\lambda_i)$. All of the previous discussion associated with attenuation matrix properties and solution strategies also applies to this embodiment.

To implement the above-described processes for monitoring channel paper levels, the invention includes various embodiments of channel power monitors. These embodiments are similar in that they all require at least one channel attenuator, detector, and analysis unit.

For embodiments in which input signals are attenuated sequentially, a variable channel attenuator having M attenuation profiles is preferred. The variable channel attenuator applies each attenuation profile characterized by $A_k(\lambda_i)$ sequentially to an input signal. Recall that k is a profile index and that $1 \leq k \leq M$.

A single detector can then be used for measuring the k-th integrated attenuated power level, the value of which is represented by $P_k$. As discussed earlier, the k-th integrated attenuated power level is the attenuated power integrated over the N signal channels after application of the k-th attenuation profile. Preferably, the detector is such that the integration of the power over the N signal channels is inherent in the properties of the detector. For instance a photodetector is typically sensitive to all light over a range of wavelengths and its output is inherently related to an integral of the incident light over the sensitive range of wavelengths. Provided that the sensitive range of wavelengths corresponds to the signal channels to be monitored, the desired integration is performed inherently by the detector. In situations where the detector does not inherently integrate the received power, the integration can be performed subsequently. In such cases, any auxiliary unit that performs the integration will be considered as part of the detector so that the outputs of the detector are the values of the integrated attenuated power levels $P_k$. Similarly, for the purposes of this document, all devices that contribute to the determination of $P_k$, from the sensing of the signals to any analog-to-digital conversion that may be required, are lumped together and called a detector.

In addition to the variable channel attenuator and the detector, the embodiment requires an analysis unit for receiving all of the values $P_k$ of the integrated attenuated power levels and deriving therefrom the values $p(\lambda_i)$ of the channel power levels by solving the following set of linear equations $$P_k = \sum_{i=1}^{N} A_k(\lambda_i) p(\lambda_i)$$

for $1 \leq k \leq M$. The analysis unit can be a digital hardware processor, an analog circuit, or a combination thereof.

For embodiments in which the input signal is split into M substantially identical scaled input signals, a variable channel attenuator is not required. What is required is a means for applying M attenuation profiles. The means can be a variable channel attenuator. Alternatively, the means can simply be M separate attenuators, each applying its own attenuation profile. Yet another option involves a number of variable channel attenuators each applying some subset of the attenuation profiles. Any other means for applying the M attenuation profiles should be considered part of the invention. For the case in which the input signal is split, multiple detectors are preferable. If M separate attenuators are used, M separate detectors would be preferable. Of course, any embodiments that involve splitting the input signal require a splitter that splits the input signal into M substantially identical scaled input signals. Each of the M scaled input signals has power represented by $r(\lambda_i)$, where $r(\lambda_i) = \alpha(\lambda_i) p(\lambda_i)$ and $\alpha(\lambda_i)$ is a known scaling function. Preferably, $\alpha(\lambda_i) = \alpha$, and is not dependent upon the channel parameter $\lambda_i$. Most preferably, $\alpha = 1/M$, but in real systems some power losses are likely to be associated with the splitting process.

In preferred embodiments of the invention the channel parameter $\lambda_i$ corresponds to wavelength. Most preferably, the system is applied to optical signals. In the most preferred embodiments, a variable optical channel attenuator (VOCA) is used as the variable channel attenuator and the detector is typically a photodetector. A VOCA is an optical device that can attenuate the power of an optical signal according to wavelength $\lambda$. When a particular attenuation profile k is applied, the VOCA functions as a transmission attenuation device.

FIG. 2 depicts the use of a VOCA 203 in a case where the signal channels are propagated in an optical system, and in particular, in an optical fiber 202. An optical signal 201 traveling through an optical fiber 202 is characterized by information coded at various wavelengths. A band window 206 (for example, C- or L-band window) spans a number of channels N, each channel with a wavelength characterized by $\lambda_i$. The signal 201 has a signal envelope 207, dictated by the channel power $p(\lambda_i)$. Various levels of power attenuation are experienced at the various wavelengths. The power at each wavelength $\lambda_i$ does not strictly follow the envelope 207. Furthermore, the incoming power at each wavelength $\lambda_i$ (i.e. each channel) is not routinely predictable.

In the case of an optical signal, the signal 201 is routed into a VOCA 203. The VOCA 203 employs a set of calibrated attenuation profiles $A_k(\lambda)$, similar to the exemplary curves depicted in FIG. 1A, or more preferably, those depicted in FIG. 1B or 1C. These attenuation profiles are characterized by $A_k(\lambda_i)$. The VOCA 203 sequentially applies the calibrated attenuation $A_k(\lambda)$ to input signals for each value of k. The attenuated output signal of the VOCA 203 is detected by a photodetector (for example, a PIN diode) 204. The photodetector 204 measures the attenuated output signal integrated across all the channel wavelengths. The value of this integrated attenuated power level is represented by $P_k$. This value is sent to an analysis unit 205. The analysis unit 205 steps the value of k in the VOCA 203 and the process is repeated for a total number of iterations M. The total power of all channels is $$P_k = \sum_{i=1}^{N} A_k(\lambda_i) p(\lambda_i)$$

where $p(\lambda_i)$ represents the values of the channel power levels. The summation is over all channels N, and $P_k$ is the measured total power when passing a VOCA with the k-th attenuation $A_k(\lambda_i)$. By obtaining N or more sets of attenuation curves and measured total powers, a set of linear equations are obtained and are solved by the analysis unit to obtain the values of the channel power levels $p(\lambda_i)$.

The above-described invention is applicable to systems in which the signal channels are wavelength-division multiplexing or dense wavelength-division multiplexing.

The above description and drawings are only illustrative of preferred embodiments, and the present invention is not intended to be limited thereto. Any modification of the present invention that comes within the spirit and scope of the following claims is considered part of the present invention.

What is claimed is:

1. A channel power monitor for monitoring channel power levels for each of N signal channels, each of the N signal channels being designated by an index i, where $1 \leq i \leq N$, and characterized by a channel parameter $\lambda_i$, each channel power level having a value designated as $p(\lambda_i)$; the channel power monitor comprising:

a variable channel attenuator having M attenuation profiles where $M \geq N$, and where a k-th attenuation profile is characterized as a function of the channel parameter $\lambda_i$ by $A_k(\lambda_i)$, k being a profile index corresponding to a particular attenuation profile and where $1 \leq k \leq M$;

a detector for measuring a k-th integrated attenuated power level, the k-th integrated attenuated power level being attenuated power integrated over the N signal channels after application of the k-th attenuation profile, the value of the k-th integrated attenuated power level being represented by $P_k$; and an analysis unit for receiving all of the values $P_k$ of the integrated attenuated power levels and deriving therefrom the values $p(\lambda_i)$ of the channel power levels by solving the following set of linear equations $$P_k = \sum_{i=1}^{N} A_k(\lambda_i)p(\lambda_i)$$

for $1 \leq k \leq M$.

2. The channel power monitor, according to claim 1, wherein the channel parameter $\lambda_i$ represents signal channel wavelength.

3. The channel power monitor, according to claim 2, wherein the variable channel attenuator is a variable optical channel attenuator and the detector is a photodetector.

4. The channel power monitor, according to claim 3, wherein the signal channels are propagated in an optical fiber.

5. The channel power monitor, according to claim 3, wherein the signal channels are propagated in an optical system.

6. The channel power monitor, according to claim 3, wherein the number of attenuation profiles M equals the number of signal channels N.

7. The channel power monitor, according to claim 3, wherein the number of attenuation profiles M exceeds the number of signal channels N.

8. The channel power monitor, according to claim 3, wherein the signal channels span the C-band.

9. The channel power monitor, according to claim 3, wherein the signal channels span the L-band.

10. The channel power monitor, according to claim 3, wherein the signal channels are wavelength-division multiplexing.

11. The channel power monitor, according to claim 3, wherein the signal channels are dense wavelength-division multiplexing.

12. The channel power monitor, according to claim 3, wherein the analysis unit is a digital hardware processor, such as a digital signal processor (DSP) or a microprocessor, an analog circuit, or a combination thereof.

13. The channel power monitor, according to claim 1, wherein the attenuation profiles are chosen to facilitate the solution of $$P_k = \sum_{i=1}^{N} A_k(\lambda_i)p(\lambda_i)$$

for $1 \leq k \leq M$.

14. The channel power monitor, according to claim 13, wherein the attenuation profiles are chosen such that a matrix A having elements $A_{ki}=A_k(\lambda_i)$ is diagonally dominant.

15. The channel power monitor, according to claim 14, wherein the attenuation profiles are chosen such that the matrix A is diagonal.

16. The channel power monitor, according to claim 1, wherein the attenuation profiles are chosen such that a matrix A having elements $A_{ki}=A_k(\lambda_i)$ is banded.

17. The channel power monitor, according to claim 16, wherein the attenuation profiles are chosen such that the matrix A is tridiagonal.

18. The channel power monitor, according to claim 1, wherein the attenuation profiles are chosen to minimize the condition number of a matrix A, where elements of matrix A are defined by $A_{ki}=A_k(\lambda_i)$ and the condition number of $$\kappa(A) = \|A\| \cdot \|A^{-1}\|$$

matrix A is defined as where $\|A\|$ is a norm of matrix A.

19. The channel power monitor, according to claim 18, wherein $\|A\|$ is the spectral norm of the matrix A.

20. A method for monitoring channel power levels of input signals for each of N signal channels, each of the N signal channels being designated by an index i, where $1 \leq i \leq N$, and characterized by a channel parameter $\lambda_i$, each channel power level having a value designated as $p(\lambda_i)$; the method comprising the steps of:

a) providing a set of M attenuation profiles, each attenuation profile characterized as a function of the channel parameter $\lambda_i$ by a k-th attenuation profile $A_k(\lambda_i)$, where $M \geq N$, and k is a profile index;

b) initializing the profile index k to a value of 1;

c) attenuating an input signal according the k-th attenuation profile $A_k(\lambda_i)$, thereby producing an attenuated power level in each signal channel;

d) measuring a k-th integrated attenuated power level, the k-th integrated attenuated power level being the attenuated power level integrated over the N signal channels after application of the k-th attenuation profile, the value of the k-th integrated attenuated power level being represented by $P_k$;

e) incrementing the profile index k by 1;

f) repeating steps c–e if $k \leq M$; and g) solving the following set of linear equations for $p(\lambda_i)$ $$P_k = \sum_{i=1}^{N} A_k(\lambda_i)p(\lambda_i)$$

for $1 \leq k \leq M$.

21. The method for monitoring channel power levels, according to claim 20, wherein the channel parameter $\lambda_i$ represents signal wavelength.

22. The method for monitoring channel power levels, according to claim 21, wherein the attenuation profiles are chosen to facilitate the solution of $$P_k = \sum_{i=1}^{N} A_k(\lambda_i)p(\lambda_i)$$

for $1 \leq k \leq M$.

23. The method for monitoring channel power levels, according to claim 21, wherein the set of M attenuation profiles are chosen such that a matrix A having elements $A_{ki}=A_k(\lambda_i)$ is diagonally dominant.

24. The method for monitoring channel power levels, according to claim 23, wherein the attenuation profiles are chosen such that the matrix A is diagonal.

25. The method for monitoring channel power levels, according to claim 21, wherein the attenuation profiles are chosen such that a matrix A having elements $A_{ki}=A_k(\lambda_i)$ is banded.

26. The method for monitoring channel power levels, according to claim 25, wherein the attenuation profiles are chosen such that the matrix A is tridiagonal.

27. The method for monitoring channel power levels, according to claim 21, wherein the attenuation profiles are chosen to minimize the condition number of a matrix A, where elements of matrix A are defined by $A_{ki}=A_k(\lambda_i)$ and $$\kappa(A) = \|A\| \cdot \|A^{-1}\|$$

where $\|A\|$ is a norm of matrix A.

28. The method for monitoring channel power levels, according to claim 27, wherein $\|A\|$ is the spectral norm of the matrix A.

29. The method for monitoring channel power levels, according to claim 20, further comprising the steps of:
   a') forming a matrix A having elements $A_{ki}=A_k(\lambda_i)$;
   a") decomposing the matrix A to facilitate the solution of the linear equations described in step g.

30. The method for monitoring channel power levels, according to claim 20, wherein the number of attenuation profiles M equals the number of signal channels N.

31. The method for monitoring channel power levels, according to claim 20, wherein the number of attenuation profiles M exceeds the number of signal channels N.

32. The method for monitoring channel power levels, according to claim 31, wherein a linear least squares method is used to minimize the error in the solution of the equations of step g.

33. A method for monitoring channel power levels for each of N signal channels, each of the N signal channels being designated by an index i, where $1 \leq i \leq N$, and characterized by a channel parameter $\lambda_i$, each channel power level having a value designated as $p(\lambda_i)$; the method comprising the steps of:
   a) providing a set of M attenuation profiles, each attenuation profile characterized as a function of the channel parameter $\lambda_i$ by a k-th attenuation profile $A_k(\lambda_i)$, where $M \geq N$, and k is a profile index;
   b) splitting an input signal into M substantially identical scaled input signals with power represented by $r(\lambda_i)$, where $r(\lambda_i)=\alpha(\lambda_i) p(\lambda_i)$ and $\alpha(\lambda_i)$ is a known scaling function;
   c) attenuating each scaled input signal according to a different attenuation profile $A_k(\lambda_i)$, thereby producing M attenuated power levels, one for each scaled input signal;
   d) measuring M integrated attenuated power levels, each integrated attenuated power level being the attenuated power level integrated over the N signal channels after application of the k-th attenuation profile, the value of the k-th integrated attenuated power level being represented by $P_k$;
   e) solving the following set of linear equations for $r(\lambda_i)$ $$P_k = \sum_{i=1}^{N} A_k(\lambda_i) r(\lambda_i)$$

for $1 \leq k \leq M$; and f) determining $p(\lambda_i)=r(\lambda_i)/\alpha(\lambda_i)$.

34. A channel power monitor for monitoring channel power levels for each of N signal channels, each of the N signal channels being designated by an index i, where $1 \leq i \leq N$, and characterized by a channel parameter $\lambda_i$, each channel power level having a value designated as $p(\lambda_i)$; the channel power monitor comprising:

a splitter for splitting an input signal into M substantially identical scaled input signals with values of power represented by $r(\lambda_i)$, where $r(\lambda_i)=\alpha(\lambda_i) p(\lambda_i)$ and $\alpha(\lambda_i)$ is a known scaling function;

a means for applying M attenuation profiles where $M \geq N$, and where a k-th attenuation profile is characterized as a function of the channel parameter $\lambda_i$ by $A_k(\lambda_i)$, k being a profile index corresponding to a particular attenuation profile and where $1 \leq k \leq M$;

at least one detector for measuring a k-th integrated attenuated power level, the k-th integrated attenuated power level being attenuated power integrated over the N signal channels after application of the k-th attenuation profile, the value of the k-th integrated attenuated power level being represented by $P_k$; and an analysis unit for receiving all of the values $P_k$ of the integrated attenuated power levels and deriving therefrom the values $r(\lambda_i)$ of the scaled input power levels by solving the following set of linear equations $$P_k = \sum_{i=1}^{N} A_k(\lambda_i) r(\lambda_i)$$

for $1 \leq k \leq M$, and subsequently determining $p(\lambda_i)=r(\lambda_i)/\alpha(\lambda_i)$.

* * * * *